US012594190B2

(12) United States Patent
Baker et al.

(10) Patent No.: US 12,594,190 B2
(45) Date of Patent: Apr. 7, 2026

(54) NONWOVEN WOUND DRESSINGS AND METHOD OF MAKING THEREOF

(71) Applicant: Solventum Intellectual Properties Company, Maplewood, MN (US)

(72) Inventors: Bryan A. Baker, Minneapolis, MN (US); Caleb T. Nelson, Woodbury, MN (US); Steven P. Swanson, Blaine, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 278 days.

(21) Appl. No.: 18/018,256

(22) PCT Filed: Aug. 3, 2021

(86) PCT No.: PCT/IB2021/057116
§ 371 (c)(1),
(2) Date: Jan. 26, 2023

(87) PCT Pub. No.: WO2022/029632
PCT Pub. Date: Feb. 10, 2022

(65) Prior Publication Data
US 2023/0255831 A1      Aug. 17, 2023

Related U.S. Application Data

(60) Provisional application No. 63/060,921, filed on Aug. 4, 2020.

(51) Int. Cl.
*A61F 13/01* (2024.01)

(52) U.S. Cl.
CPC .............................. *A61F 13/01034* (2024.01)

(58) Field of Classification Search
CPC .... A61F 13/00; A61F 13/0206; A61F 13/023; A61F 13/00008; A61F 13/02; A61F 13/00012; A61F 13/00034; A61F 13/01034; A61F 13/01046; A61F 2013/00089; A61F 2013/00744; A61F 2013/15934; A61F 2013/53062; D04H 1/4258; D04H 1/492; D06M 10/02; D06M 10/025
USPC ...................................... 602/41–43, 45, 900
See application file for complete search history.

(56) References Cited

U.S. PATENT DOCUMENTS

| | | | |
|---|---|---|---|
| 4,472,480 A | 9/1984 | Olson | |
| 6,309,454 B1 | 10/2001 | Harvey et al. | |
| 2010/0074858 A1* | 3/2010 | Messier | A01N 59/12 521/30 |
| 2016/0038626 A1 | 2/2016 | Locke et al. | |
| 2019/0134243 A1 | 5/2019 | Nelson et al. | |

FOREIGN PATENT DOCUMENTS

| | | | |
|---|---|---|---|
| CN | 110273298 A * | 9/2019 | D06M 15/263 |
| CN | 111041604 A | 4/2020 | |
| CN | 111405740 A | 7/2020 | |

(Continued)

OTHER PUBLICATIONS

CN 110273298 A machine translation (Year: 2019).*

(Continued)

*Primary Examiner* — Caitlin A Carreiro

(57) ABSTRACT

An article. The article includes a nonwoven having a pH value from 2 to 6; wherein the article is a wound dressing.

8 Claims, 1 Drawing Sheet

430

410

(56)  References Cited

FOREIGN PATENT DOCUMENTS

| CN | 111424428 | A | | 7/2020 | | |
|----|-----------|---|---|--------|---|---|
| EP | 2873531 | A1 | * | 5/2015 | .......... | B41M 5/0011 |
| KR | 20170002463 | A | * | 1/2017 | .......... | G01N 21/255 |
| WO | 1998000180 | A1 | | 1/1998 | | |
| WO | WO-2015061079 | A1 | * | 4/2015 | ........... | D06M 10/10 |

OTHER PUBLICATIONS

KR20170002463A machine translation (Year: 2017).*
Cullen, "Mechanism of Action of Promogran, A Protease Modulating Matrix, for the Treatment of Diabetic Foot Ulcers", 2002, Wound Repair and Regeneration, vol. 10, No. 1, pp. 16-25.
Greener, "Proteases and pH in Chronic Wounds", 2005, Journal of Wound Care, vol. 14, No. 2, pp. 59-61.
International Search Report received for PCT International Application No. PCT/IB2021/057116, mailed on Nov. 22, 2021, 4 pages.

* cited by examiner

NONWOVEN WOUND DRESSINGS AND METHOD OF MAKING THEREOF

CROSS REFERENCE TO RELATED APPLICATIONS

This application is a national stage filing under 35 U.S.C. 371 of PCT/IB2021/057116, filed Aug. 3, 2021, which claims the benefit of Provisional Application No. 63/060,921, filed Aug. 4, 2020, the disclosure of which is incorporated by reference in its/their entirety herein.

BACKGROUND

Wound dressings, including nonwoven based dressings, are applied in the treatment of chronic wounds to promote a healing environment in the wound. There is a need to provide better dressings in a form useful for treating wounds.

SUMMARY

Thus, in one aspect, the present disclosure provides an article comprising, a nonwoven having a pH value from 2 to 6; wherein the article is a wound dressing.

In another aspect, the present disclosure provides a method of making an article, comprising: providing a nonwoven; reducing pH value of the nonwoven by a first plasma treatment; wherein the article is a wound dressing.

Various aspects and advantages of exemplary embodiments of the present disclosure have been summarized. The above Summary is not intended to describe each illustrated embodiment or every implementation of the present disclosure. Further features and advantages are disclosed in the embodiments that follow. The Drawings and the Detailed Description that follow more particularly exemplify certain embodiments using the principles disclosed herein.

Definitions

For the following defined terms, these definitions shall be applied for the entire Specification, including the claims, unless a different definition is provided in the claims or elsewhere in the Specification based upon a specific reference to a modification of a term used in the following definitions: The terms "about" or "approximately" with reference to a numerical value or a shape means +/–five percent of the numerical value or property or characteristic, but also expressly includes any narrow range within the +/–five percent of the numerical value or property or characteristic as well as the exact numerical value. For example, a temperature of "about" 100° C. refers to a temperature from 95° C. to 105° C., but also expressly includes any narrower range of temperature or even a single temperature within that range, including, for example, a temperature of exactly 100° C. For example, a viscosity of "about" 1 Pa-sec refers to a viscosity from 0.95 to 1.05 Pa-sec, but also expressly includes a viscosity of exactly 1 Pa-sec. Similarly, a perimeter that is "substantially square" is intended to describe a geometric shape having four lateral edges in which each lateral edge has a length which is from 95% to 105% of the length of any other lateral edge, but which also includes a geometric shape in which each lateral edge has exactly the same length.

The term "substantially" with reference to a property or characteristic means that the property or characteristic is exhibited to a greater extent than the opposite of that property or characteristic is exhibited. For example, a substrate that is "substantially" transparent refers to a substrate that transmits more radiation (e.g. visible light) than it fails to transmit (e.g. absorbs and reflects). Thus, a substrate that transmits more than 50% of the visible light incident upon its surface is substantially transparent, but a substrate that transmits 50% or less of the visible light incident upon its surface is not substantially transparent.

The terms "a", "an", and "the" include plural referents unless the content clearly dictates otherwise. Thus, for example, reference to a material containing "a compound" includes a mixture of two or more compounds.

BRIEF DESCRIPTION OF THE DRAWINGS

The disclosure may be more completely understood in consideration of the following detailed description of various embodiments of the disclosure in connection with the accompanying figures, in which.

Figure 1:
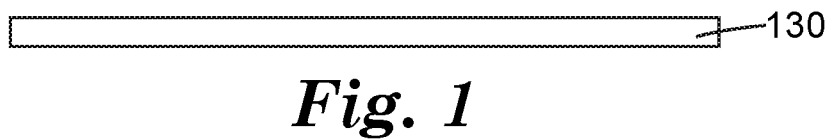
FIG. 1 is a schematic cross-section of an illustrative embodiment of an article suitable for a wound dressing in the form of a sheet.

While the above-identified drawings, which may not be drawn to scale, set forth various embodiments of the present disclosure, other embodiments are also contemplated, as noted in the Detailed Description. In all cases, this disclosure describes the presently disclosed invention by way of representation of exemplary embodiments and not by express limitations. It should be understood that numerous other modifications and embodiments can be devised by those skilled in the art, which fall within the scope and spirit of this disclosure.

DETAILED DESCRIPTION

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

As used in this Specification, the recitation of numerical ranges by endpoints includes all numbers subsumed within that range (e.g. 1 to 5 includes 1, 1.5, 2, 2.75, 3, 3.8, 4, and 5, and the like).

Unless otherwise indicated, all numbers expressing quantities or ingredients, measurement of properties and so forth used in the Specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The articles and methods of the description are useful as wound dressings and in the healing of wounds (both acute and chronic). Without wishing to be bound by theory, the articles and methods of the description are believed to improve wound healing in part by lowering the pH of the wound environment.

Lowering the pH of the wound environment (such as the exposed wound surface and wound fluid) can improve wound healing by reducing detrimental protease activity in a wound; inhibiting the growth of pathogenic bacteria in an infected wound; and increasing oxygen levels in wound tissue. Outcomes of improved wound healing can include faster wound healing and\or more complete wound healing.

In some embodiments, an article is described. The article can be a wound dressing. The article can include a nonwoven having a pH value from 2 to 6. In some embodiments, the nonwoven has a pH value from 2 to 6, from 3 to 6, from 2 to 5, from 3 to 5, from 2 to 4.5, from 2 to 4, or from 2 to 3. The nonwoven can be plasma treated.

In some embodiments, a method of forming an article is described. The method comprises providing a nonwoven and reducing the pH value of the nonwoven by a first plasma treatment. In some embodiments, the article is a wound dressing. In some embodiments, the first plasma treatment is substantially at atmospheric pressure. In some embodiments, the first plasma treatment can include introducing an input gas comprising oxygen, nitrogen, and water vapor. In some embodiments, the method can include a second plasma treatment after the first plasma treatment. In some embodiments, the second plasma treatment can include introducing an oxygen plasma at sub atmospheric pressure.

Any suitable sources of nonwoven can be used. Nonwoven materials can include, for example, rayon, cellulose, viscose, cotton, polyethylene terephthalate, polypropylene, polyurethane, and others. Nonwoven can include articles made from the processes of spunlaid, spunbond, spunlaced, airlaid, wetlaid, carded and melt-blown.

In typical embodiments, a plasma treatment is used to reduce the pH value of a nonwoven to a desired pH range. In some embodiments, the nonwoven has a pH value from 2 to 6, from 3 to 6, from 2 to 5, from 3 to 5, from 2 to 4.5, from 2 to 4, or from 2 to 3. In some embodiments, the nonwoven has a pH value less than 6, 5, 4.5, 4, 3.5, 3, or 2.5. In some embodiments, the nonwoven has a pH value greater than 1.2, 1.5, 1.8, 1.9, 2, 2.5, 3, or 3.5. Any suitable plasma treatment can be used. Plasma treatment refers to the use of an electrical discharge applied to a liquid or gaseous medium. Plasma treatment can be carried out at in either atmospheric or sub-atmospheric conditions, for example, as described in US 2019/0134243 A1 (Nelson et al.). Exposure of the nonwoven can take place either in direct contact with the plasma or in a downstream location. Energy is applied in the form of coupled electrical power to the liquid or gaseous medium creating new reactive species to interact with the nonwoven. Typical plasma treatments create oxidizing and/or acidic species. In some embodiments, the applied energy density is greater than 0.05 eV/molecule of the gas passing through the plasma.

The pH of the nonwoven can be determined according to 'pH Test Method A' (described in the Examples Section).

A low pH nonwoven dressing can provide advantages for wound healing, for example, the nonwoven dressing can affect the function of some enzymes, such as proteases, which if unchecked lead to the breakdown of tissue, perpetuating the wounded state.

The wound dressing article described herein comprises a nonwoven in a suitable physical form such as a sheet, fibers, mat, scaffold, or nonwoven disposed on or within a carrier layer.

Figure 2:
FIG. 2 is a schematic cross-section of an illustrative embodiment of an article suitable for a wound dressing comprising a carrier layer.

In some embodiments, the nonwoven is formed prior to combining the nonwoven with a carrier material or carrier layer. FIGS. 1-2 as follow illustrative some typical wound dressings articles.

FIG. 1 illustrates an embodiment of a wound dressing article. The wound dressing article includes a (e.g. flexible) sheet 130 comprising or consisting of the (e.g. dehydrated) nonwoven having a pH value from 2 to 6.

The wound dressing article articles, such as illustrated in FIG. 1 typically have a thickness of at least 0.4 mm, 0.5 mm, 0.6 mm, or 0.7 mm and typically no greater than 12 mm, 10 mm, 7 mm, 5 mm, 4 mm, 3 mm, 2 mm, or 1 mm.

The embodiment of FIG. 1 may further comprise a carrier layer disposed on a major surface of the nonwoven. A carrier layer is typically disposed on the opposing major surface as the wound-facing surface. For example, FIG. 2 illustrates an embodiment of a wound dressing article. The wound dressing article includes a sheet 430 comprising or consisting of the nonwoven and a carrier layer 410.

In some embodiments, carrier layer 410 is a release liner. The release liner carrier may be disposed on the opposing major surface of both major surfaces (not shown) such that the nonwoven is between the release liner layers.

Various release liners are known such as those made of (e.g. kraft) papers, polyolefin films such as polyethylene and polypropylene, or polyester. The films are preferably coated with release agents such as fluorochemicals or silicones. For example, U.S. Pat. No. 4,472,480 describes low surface energy perfluorochemical liners. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films commercially available from H. P. Smith Co. and fluoropolymer coated polyester films commercially available from 3M under the brand "ScotchPak™" release liners.

In other embodiments, the carrier layer 410 may comprise a variety of other (e.g. flexible and/or conformable) carrier materials such as polymeric films and foams as well as various nonwoven and woven fibrous materials, such as gauze. In some embodiments, the carrier layer is absorbent, such as an absorbent foam. In other embodiments, the carrier layer is non-absorbent, such as a polymeric film.

In some embodiments, a method of treating a wound with an article of the disclosure is described. The method of treatment involves covering at least a portion of the wound with the article. At least a portion of the wound surface or wound fluid can be in contact with the nonwoven portion of the article. In some embodiments, the method of treatment changes the pH of the wound environment. The wound environment includes the wound surface and the wound fluid. In some embodiments, the method of treatment decreases the pH of the wound environment. In some embodiments, the method of treatment decreases the pH of at least a portion of the wound surface. In some embodiments, the method of treatment decreases the pH of the wound fluid.

The wound to be treated by the method can be an open wound of the skin that exposes underlying body tissue. An open wound typically contains a wound fluid. Open wounds that can be treated by the method include acute wounds and chronic wounds.

The wound environment of a chronic wound (including the wound fluid) is often alkaline with a pH ranging from about 7.2-9. Wounds having an alkaline pH are known to have lower rates of healing than wounds having an acidic pH.

Open wounds that can be treated by the method include wounds to the skin from trauma (for example avulsions, incisions, and lacerations); wounds to the skin from pressure (for example pressure ulcers); and wounds to the skin from disease (for example venous ulcers, diabetic foot ulcers, and diabetic leg ulcers). In some embodiments, the wound environment is the exposed area of an open wound.

In some embodiments, the method of treatment changes the pH of the wound environment from alkaline to acidic. In some embodiments, the method of treatment changes the pH of the wound environment from greater than pH 7 to less than pH 7. In some embodiments, the method of treatment changes the pH of the wound environment from greater than pH 7 to either pH 3-6.8, pH 4-6.8, pH 4.5-6.8, pH 4-6.5, or pH 4.5-6.5.

In some embodiments, the method of treatment changes the pH of the wound fluid from alkaline to acidic. In some embodiments, the method of treatment changes the pH of the wound fluid from greater than pH 7 to less than pH 7. In some embodiments, the method of treatment changes the pH of the wound fluid from greater than pH 7 to either pH 3-6.8, pH 4-6.8, pH 4.5-6.8, pH 4-6.5, or pH 4.5-6.5.

In some embodiments, the method of treatment causes the pH of the wound environment to be from 3-6.9. In some embodiments, the method of treatment causes the pH of the wound environment to be from 3-6.8. In some embodiments, the method of treatment causes the pH of the wound environment to be from pH 4-6.8. In some embodiments, the method of treatment causes the pH of the wound environment to be from pH 4.5-6.8. In some embodiments, the method of treatment causes the pH of the wound environment to be from pH 4-6.5.

In some embodiments, the method of treatment causes the pH of the wound fluid to be from 3-6.9. In some embodiments, the method of treatment causes the pH of the wound fluid to be from 3-6.8. In some embodiments, the method of treatment causes the pH of the wound fluid to be from pH 4-6.8. In some embodiments, the method of treatment causes the pH of the wound fluid to be from pH 4.5-6.8. In some embodiments, the method of treatment causes the pH of the wound fluid to be from pH 4-6.5.

In another embodiment, the present disclosure provides a method of using a wound dressing article, with the method comprising contacting at least a portion of the nonwoven of a wound dressing article of the present disclosure with an exposed surface of a wound. The wound dressing article can have a nonwoven with a pH value from 2-6. The wound can be an open wound. The wound can be a chronic wound. In some embodiments the method of using a wound dressing article can cause the pH of the wound environment to change from alkaline to acidic. In some embodiments the method of using a wound dressing article can cause the pH of the wound environment to decrease. In some embodiments the method of using a wound article can cause the pH of the wound environment to be from 3-6.9, from 3-6.8, from 4-6.9, from 4-6.8, from 4.5-6.8, from 4-6.5, or from 4.5-6.5.

In another embodiment, the present disclosure provides a method of using a wound dressing article, with the method comprising contacting at least a portion of the nonwoven of a wound dressing article of the present disclosure with the wound fluid of a wound. The wound can be an open wound. The wound can be a chronic wound. The wound dressing article can have a nonwoven with a pH value from 2-6. In some embodiments the method of using a wound dressing article can cause the pH of the wound fluid to change from alkaline to acidic. In some embodiments the method of using a wound dressing article can cause the pH of the wound fluid to decrease. In some embodiments the method of using a wound article can cause the pH of the wound fluid to be from 3-6.9, from 3-6.8, from 4-6.9, from 4-6.8, from 4.5-6.8, from 4-6.5, or from 4.5-6.5.

The pH of a wound environment or wound fluid can be measured using pH paper, a pH electrode, a pH microelectrode, or any other suitable pH sensor.

The following working examples are intended to be illustrative of the present disclosure and not limiting.

EXAMPLES

Methods
Plasma Method A. Atmospheric Plasma Treatment of a Nonwoven Sample

Nonwoven samples were treated using an atmospheric plasma system of the design described in in United States Patent Application No. 20190134243, incorporated herein by reference in its entirety. After the plasma generator, the effluent was transported through a six foot (1.83 meter) length of polytetrafluoroethylene (PTFE) tubing with a ⅛ inch (3.17 millimeter) diameter inner lumen. The lumen was adapted with a stainless steel adaptor to a % inch (6.35 mm) inner diameter (ID) PTFE sample tube that was eight inches (20.32 cm) in length. The sample tube was reduced to 3/16 inch (4.76 mm) on the atmospheric side. Nonwoven samples were loaded into the middle of the sample tube. After the samples were loaded in the sample tube, room air was introduced to the plasma electrode at a rate of 3 standard liter per minute (SLM). The gas precursor was humidified with vaporized water to 40% relative humidity (RH) at room temperature. Power was coupled to the plasma electrode from a 12 kHz ac power supply with a voltage of 3.6 kV and a total power of 85 W for a specified exposure time. At the end of the exposure, the power was turned off and samples were removed from the system.
Plasma Method B. Sub-Atmospheric (Vacuum) Plasma Treatment of a Nonwoven Sample Nonwoven samples were treated in an oxygen plasma using a Plasma-Therm 3032 batch plasma reactor (obtained from Plasma-Therm LLC, St. Petersburg, FL). The instrument was configured for reactive ion etching with a 26 inch (66 cm) lower powered electrode and central gas pumping. The chamber was pumped with a roots type blower (model EH1200 obtained from Edwards Engineering, Burgess Hill, UK)) backed by a dry mechanical pump (model iQDP80 obtained from Edwards Engineering). The RF power was delivered by a 3 kW, 13.56 Mhz solid-state generator (RFPP model RF30S obtained from Advanced Energy Industries, Fort Collins, CO). The system had a nominal base pressure of 5 mTorr. The flow rates of the gases were controlled by MKS flow controllers (obtained from MKS Instruments, Andover, MA).

Samples were fixed on the powered electrode of the plasma reactor. After pumping down to the base pressure, oxygen was introduced at 500 standard cubic centimeters per minute (SCCM). Once the gas flow stabilized in the reactor, rf power (1000 watts) was applied to the electrode to generate the plasma. The plasma was ignited for the specified treatment time. Following completion of the plasma treatment, the chamber was vented to the atmosphere and the sample was removed from the chamber. Both sides of the nonwoven were treated. Treatment of the second side involved the same steps as described above with the sample flipped over on the powered electrode.

pH Test Method A. pH Measurement of Nonwoven

A 10 mg/mL suspension of the nonwoven sample was prepared in distilled water. The pH of the distilled water before the addition of the nonwoven sample was 6.8-7.2. The water was maintained at 25° C. and the nonwoven sample was completely immersed in the water. Following immersion for one minute, the pH value of the water was measured using a calibrated pH meter.

EXAMPLES

Example 1

A plasma treatment according to Plasma Method A (described above) was applied to a sample of an SX-984 spunlaced lyocell nonwoven sheet (50 gsm basis weight and 0.75 mm thickness, obtained under the product code #GB000SX984 from Suominen, Helsinki, Finland). The plasma exposure time was 120 seconds.

Example 2

A first plasma treatment according to Plasma Method A (described above) was applied to a 10 mg sample of an SX-984 spunlaced lyocell nonwoven sheet (50 gsm basis weight and 0.75 mm thickness, obtained under the product code #GB000SX984 from Suominen, Helsinki, Finland). The plasma exposure time was 120 seconds. The resulting sample was submitted to a second plasma treatment according to Plasma Method B (described above). Each side of the nonwoven sample was plasma treated for 60 seconds.

Example 3

A plasma treatment according to Plasma Method A (described above) was applied to a 10 mg sample of a nonwoven rayon sheet (50 gsm basis weight, obtained from Fitesa, Simpsonville, SC). The plasma exposure time was 120 seconds.

Example 4

A first plasma treatment according to Plasma Method A (described above) was applied to a 10 mg sample of a nonwoven rayon sheet (50 gsm basis weight, obtained from Fitesa, Simpsonville, SC). The plasma exposure time was 120 seconds. The resulting sample was submitted to a second plasma treatment according to Plasma Method B (described above). Each side of the nonwoven sample was plasma treated for 60 seconds.

Example 5. pH Measurements of Nonwoven Samples Prepared by Examples 1-4

The pH of each plasma treated nonwoven sample prepared in Examples 1-4 was measured according to pH Test Method A (described above). The pH of the water was measured using a VWR SYMPHONY pHconductivity meter (model #B30PCI, obtained from the VWR Corporation, Radnor, PA). The results are presented in Table 1. The results show that each plasma treated nonwoven sample lowered the pH of the water media.

TABLE 1

| Measured pH after Immersion of Nonwoven in Water for 1 Minute (pH Test Method A) | |
| --- | --- |
| Nonwoven Sample | Measured pH of Water Media |
| Example 1 | 4 |
| Example 2 | 3.5 |
| Example 3 | 4 |
| Example 4 | 2.5 |

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A method of making an article, comprising
   providing a nonwoven;
   reducing pH value of the nonwoven by a first plasma treatment comprising introducing at atmospheric pressure an input gas comprising oxygen, nitrogen, and water vapor; and
   treating the nonwoven with a second plasma treatment after the first plasma treatment, wherein the second plasma treatment comprises introducing an oxygen plasma at sub atmospheric pressure;
   wherein the article is a wound dressing comprising the nonwoven.

2. The method of claim 1, further comprising incorporating a carrier into the article.

3. The method of claim 2, wherein the nonwoven is disposed on or within the carrier.

4. The method of claim 1, wherein the nonwoven has a pH value from 2 to 5.

5. The method of claim 1, wherein the nonwoven has a pH value from 2 to 4.

6. The method of claim 1, wherein the nonwoven comprises lyocell or rayon.

7. The method of claim 1, further comprising incorporating a substrate into the article.

8. The method of claim 1, wherein the nonwoven is a sheet, fibers, mat, or scaffold.

* * * * *